United States Patent [19]

Coffee

[11] Patent Number: 5,006,546
[45] Date of Patent: Apr. 9, 1991

[54] IMIDAZOLE DERIVATIVES

[75] Inventor: Edward C. J. Coffee, Upminster, England

[73] Assignee: Rhone-Poulenc Sante, Antony, France

[21] Appl. No.: 498,628

[22] Filed: Mar. 26, 1990

[30] Foreign Application Priority Data

Apr. 5, 1989 [GB] United Kingdom ............... 8907656

[51] Int. Cl.⁵ .................. C07D 405/12; A61K 31/415
[52] U.S. Cl. .................................... 514/397; 548/336
[58] Field of Search ......................... 548/336; 514/397

[56] References Cited

U.S. PATENT DOCUMENTS 3,714,179  1/1973  Tweit .................................. 548/336
4,402,960  9/1983  Niedballa et al. ................... 548/336
4,421,758  12/1983  Kawamoto et al. ................ 548/336

FOREIGN PATENT DOCUMENTS 2038825  7/1980  United Kingdom ............... 514/397

Primary Examiner—Mary C. Lee
Assistant Examiner—Lenora Miltenberger
Attorney, Agent, or Firm—Morgan & Finnegan

[57] ABSTRACT

The invention provides: (2S,4R,6S)-6-[(4,5-diphenylimidazol-2-yl)thiomethyl]-4-hydroxy-2-methoxy-3,4,5,6-tetrahydro-2H-pyran and (2R,4R,6S)-6-[(4,5-diphenylimidazol-2-yl)thiomethyl]-4-hydroxy-2-methoxy-3,4,5,6-tetrahydro-2H-pyran or a mixture thereof; the compounds are anti-atherosclerotic agents.

3 Claims, No Drawings

IMIDAZOLE DERIVATIVES

This invention relates to new, therapeutically useful imidazole derivatives, to a process for their production and to pharmaceutical compositions containing them.

The new imidazole derivatives of the present invention are the compounds of formulae (I) and (II) hereinafter depicted.

The compounds according to the invention are:
(I). (2S,4R,6S)-6-[(4,5-diphenylimidazol-2-yl) thiomethyl]-4-hydroxy-2-methoxy-3,4,5,6-tetrahydro-2H-pyran; and
(II). (2R,4R,6S)-6-[(4,5-diphenylimidazol-2-yl) thiomethyl]-4-hydroxy-2-methoxy-3,4,5,6-tetrahydro-2H-pyran.

The invention also encompasses mixtures of compounds (I) and (II).

The compounds according to the invention are inhibitors of acyl coenzyme-A:cholesterol-O-acyl transferase (ACAT;EC 2.3.1.26). They are therefore of value as anti-antherosclerotic agents and have utility in the treatment of atherosclerosis, hyperlipidaemia, cholesterol ester storage disease and atheroma in vein grafts.

In in-vitro tests, using microsomes obtained from the livers of rats fed on a diet containing 0.5% w/w cholesterol and 0.25% w/w cholic acid, the compounds according to the invention were found to give $IC_{50}$ figures as shown in Table I, wherein $IC_{50}$ is the concentration required to produce a 50% inhibition in the activity of acyl coenzyme-A:cholesterol-O-acyl transferase.

TABLE 1

| Compound | $IC_{50}$ (nM) |
|---|---|
| (I) | 50 |
| (II) | 91 |

According to a feature of the invention, the compounds of formulae (I) and (II) are made by the desilylation of compounds of formula (III), in which $R^1$, $R^2$, and $R^3$, which can be identical or different, each represent a straight or branched-chain alkyl group containing 1 to 4 carbon atoms, or an optionally substituted phenyl group (the optional substituent being one which is inert to the reaction conditions and which does not cause any reaction other than the desilylation to occur). This is carried out by a conventional reagent such as an ammonium fluoride (e.g. tetrabutylammonium fluoride) in an anhydrous, inert solvent (e.g. an ether, such as tetrahydrofuran), preferably at room temperature. For example the group $SiR^1R^2R^3$ can be the t-butyldimethylsilyl group.

Compounds of formula (III) constitute a further feature of the invention.

Compounds of formula (III) are made by the reaction of the compounds of formula (IV), wherein $R^1$, $R^2$, and $R^3$ are as hereinabove defined, with the compound of formula (V). This reaction is carried out, preferably under dry conditions, in the presence of a base, such as potassium carbonate, optionally under an inert atmosphere (e.g. argon), in an inert solvent, such as dimethylsulphoxide, optionally with heating (e.g. up to 60° C.).

This reaction may result in epimerisation at the methoxy-bearing carbon atom and as a result the desilylation reaction which gives the compounds of formulae (I) and (II) may produce an anomeric mixture. Compounds (I) and (II) can be separated by conventional means, such as chromatography over silica gel using a suitable eluant.

The compounds of formula (IV) may be made by the method of T. Rosen et.al. [J.Org.Chem, (1984), 49, 3994].

Compounds of formulae (I) and (II) can be purified by the usual physical mans, for example by crystallisation or chromatography.

The following Examples illustrate the preparation of the compounds according to the invention and the Reference Example illustrates the preparation of the intermediates of formula (III).

All N.M.R. spectra were recorded at 200 MHz. Chemical shifts are expressed in ppm relative to tetramethylsilane. Abbreviations have the following significances:
s = singlet
ss = singlets
d = doublet
t = triplet
m = multiplet

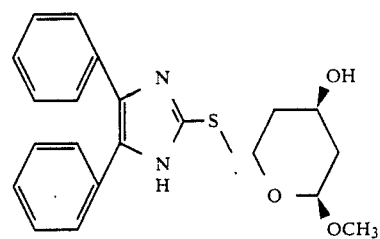

I

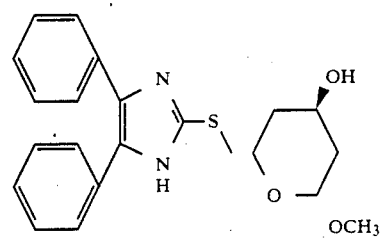

II

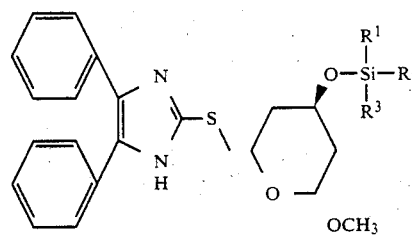

III

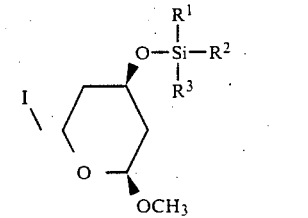

IV

-continued

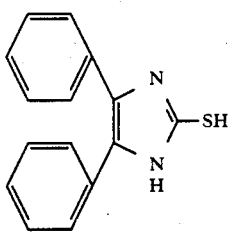

V

EXAMPLE 1

Compounds (I) and (II)

A solution of a mixture of (2S,4R,6S)-4-t-butyldimethylsilyloxy-6-[(4,5-diphenylimidazol-2-yl)-thiomethyl]-2-methoxy-3,4,5,6-tetrahydro-2H-pyran and (2R,4R,6S)-4-t-butyldimethylsilyloxy-6-[(4,5-diphenylimidazol-2-yl) thiomethyl]-2-methoxy-3,4,5,6-tetrahydro-2H-pyran (3.5 g), in dry tetrahydrofuran (70 ml), was treated with a solution of tetrabutylammonium fluoride in tetrahydrofuran, 1.0 M; 100 ml) and the mixture was left to stand at room temperature for 18 hours. The solution was then poured into water, and was extracted with ethyl acetate. The combined extracts were washed with water, then dried over magnesium sulphate, and were concentrated at reduced pressure to give a gum (4.04 g). This was chromatographed on silica gel, eluting with a mixture of ethyl acetate and hexane (3:1 v/v), to give: (2S,4R,6S)-6-[(4,5-diphenylimidazol-2-yl) thiomethyl]-4-hydroxy-2-methoxy-3,4,5,6-tetrahydro-2H-pyran (1.74 g), in the form of a white solid, m.p. 80°–108° C.

[N.M.R. (CDCl$_3$): 1.26 (1.5H, t), 1.65–2.02 (4H, m), 2.4 (1.5H, s), 3.06–3.6 (2H, m), 3.46 (3H, s), 4.06–4.2 (2H, m), 4.35–4.5 (1H, m), 4.9 (1H, d), 7.1–7.8 (10H, m), 10.46 (1H, s);

Elemental analysis: C, 65.3, H, 6.1, N, 6.7, S, 7.7%;

Calculated for $C_{22}H_{24}N_2SO_3,0.5CH_3COOC_2H_5$: C, 65.43, H, 6.41, N, 6.36, S, 7.28%]; and (2R,4R,6S)-6-[(4,5-diphenylimidazol-2-yl) thiomethyl]-4-hydroxy-2-methoxy-3,4,5,6-tetrahydro-2H-pyran (0.27 g), in the form of a white solid, m.p. 202°–203° C.

[N.M.R. (CDCl$_3$): 1.26 (0.75H, t), 1.5–1.75 (2H, m), 1.8–2.0 (2H, m), 2.4 (0.75H, s), 3.1–3.5 (2H, m), 3.38 (3H, s), 4.0–4.4 (3.5H, m), 4.81 (1H, dd), 7.0–7.8 (10H, m);

Elemental analysis: C, 65.6, H, 6.07, N, 6.79, S, 7.7%.

Calculated for $C_{22}H_{24}N_2SO_3,0.25CH_3COOC_2H_5$: C, 66.00, H, 6.26, N, 6.70, S, 7.66%].

REFERENCE EXAMPLE

Compound (III)

A mixture of 4,5-diphenyl-2-mercaptoimidazole, (3.61 g), (2S,4R,6S)-4-t-butyldimethylsilyoxy-6-iodomethyl-2-methoxy-3, 4,5,6-tetrahydro-2H-pyran (3.7 g), and anhydrous potassium carbonate (4.02 g), was stirred and heated at 60° under argon in dry dimethylsulphoxide (60 ml) for 4.5 hours. The mixture was cooled and poured into water (400 ml), and was extracted with ethyl acetate (4×100 ml). The ethyl acetate extract was washed with water, brine, and was dried over magnesium sulphate. The extract was concentrated under reduced pressure to give an oil which was chromatographed on silica gel, eluting with a mixture of hexane and ethyl acetate (4:1 v/v), to give a mixture of (2S,4R,6S)-4-t-butyldimethylsilyloxy-6-(4,5-diphenylimidazol-2-yl)thiomethyl]-2-methoxy-3,4,5,6-tetrahydro-2H-pyran and (2R,4R,6S)-4-t-butyldimethylsilyloxy-6-[(4,5-diphenylimidazol-2-yl) thiomethyl]-2-methoxy-3,4,5,6-tetrahydro-2H-pyran (3.58 g) in the form of a gum.

[N.M.R. (CDCl$_3$): 0.2, 0.3 (6H, 2s), 0.9 (9H, ss) 1.5–1.9 (4H, m), 2.95–3.3 (2H, m), 3.1 (2.6H, s), 3.20 (0.4H, s), 4.42–4.6 (1H, m), 4.8–4.9 (1H, m), 7.1–7.7 (10H, m)[.

The present invention also includes within its scope pharmaceutical formulations which comprise the compound(s) of formula(e) (I) and/or (II) in association with a pharmaceutically acceptable carrier or coating. In clinical practice the compounds of the present invention may be administered parenterally, rectally or orally.

Solid compositions for oral administration include compressed tablets, pills, powders and granules. In such solid compositions, one or more of the active compounds is, or are, admixed with at least one inert diluent such as starch, sucrose or lactose. The compositions may also comprise, as is normal practice, additional substances other than inert diluents, e.g. lubricating agents, such as magnesium stearate.

Liquid compositions for oral administration include pharmaceutically acceptable emulsions, solutions, suspensions, syrups and elixirs containing inert diluents commonly used in the art such as water and liquid paraffin. Besides inert diluents such compositions may comprise adjuvants, such as wetting and suspending agents, and sweetening, flavouring, perfuming and preserving agents. The compositions according to the invention for oral administration also include capsules of absorbable material such as gelatin, containing one or more of the active substances with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. The compositions may also contain adjuvants such as stabilising, preserving, wetting, emulsifying and dispersing agents. They may be sterilised, for example, by filtration through a bacteria-retaining filter, by incorporation in the compositions of sterilising agents, by irradiation or by heating. They may also be manufactured in the form of sterile solid compositions, which can be dissolved in sterile water or some other sterile injectable medium immediately before use.

Solid compositions for rectal administration include suppositories formulated in accordance with known methods and containing the compound(s) of formula(e) I and/or (II).

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from 0.5 to 70, preferably 1 to 10, mg/kg body weight per day by oral administration.

The following Example illustrates pharmaceutical compositions according to the present invention.

COMPOSITION EXAMPLE 1

No. 2 size gelatin capsules each containing:

| COMPOSITION EXAMPLE 1 | |
|---|---|
| No. 2 size gelatin capsules each containing: | |
| (2S,4R,6S)-6-[(4,5-diphenylimidazol-2-yl)thiomethyl]-4-hydroxy-2-methoxy-3,4,5,6-tetrahydro-2H-pyran | 20 mg |
| lactose | 100 mg |
| starch | 60 mg |
| dextrin | 40 mg |
| magnesium stearate | 1 mg | were prepared in accordance with the usual procedure.

I claim:

1. An imidazole derivative which is: (2S,4R,6S)-6-[(4,5-diphenylimidazol-2-yl)thiomethyl]-4-hydroxy-2-methoxy-3,4,5,6-tetrahydro-2H-pyran or (2R,4R,6S)-6-[(4,5-diphenylimidazol-2-yl)thiomethyl]-4-hydroxy-2-methoxy-3,4,5,6-tetrahydro-2H-pyran or a mixture thereof.

2. A pharmaceutical composition useful for the treatment of atherosclerosis, hyperlipidaemia, cholesterol ester storage, and atheroma in vein grafts, said composition comprising an amount effective for the purposes indicated of (2S, 4R, 6S)-6-[(4,5-diphenylimidazol-2-yl)thiomethyl]-4-hydroxy-2-methoxy-3,4,5,6-tetrahydro-2H-pyran or (2R,4R,6S)-6-[(4,5-diphenylimidazol-2-yl)thiomethyl]-4-hydroxy-2-methoxy-3,4,5,6-tetrahydro-2H-pyran or a mixture thereof, in association with a pharmaceutically acceptable carrier or coating.

3. A method of treating a human or animal showing the symptoms of atherosclerosis, hyperlipidaemia, cholesterol ester storage disease, or atheroma in vein grafts, comprising the administration to a human or animal in need of such treatment an effective amount of (2S, 4R, 6S)-6-[(4,5-diphenylimidazol-2-yl) thiomethyl]-4-hydroxy-2-methoxy-3,4,5,6-tetrahydro-2H-pyran or (2R,4R,6S,)-6-[(4,5-diphenylimidazol-2-yl) thiomethyl]-4-hydroxy-2-methoxy-3,4,5,6-tetrahydro-2H-pyran or mixtures thereof.

* * * * *